US007887818B2

(12) United States Patent
Tuo et al.

(10) Patent No.: US 7,887,818 B2
(45) Date of Patent: Feb. 15, 2011

(54) *NEOSPORA CANINUM* VACCINE

(75) Inventors: Wenbin Tuo, Clarksville, MD (US);
Mark C. Jenkins, Davidsonville, MD (US); Yan Zhao, Herndon, VA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/070,684

(22) Filed: Feb. 20, 2008

(65) Prior Publication Data
US 2009/0208519 A1    Aug. 20, 2009

(51) Int. Cl.
*A61K 39/012* (2006.01)
*C07K 14/00* (2006.01)

(52) U.S. Cl. .............. 424/265.1; 424/184.1; 424/269.1; 530/350

(58) Field of Classification Search ........................ None
See application file for complete search history.

(56) References Cited

U.S. PATENT DOCUMENTS 6,951,651 B2 * 10/2005 Diamond ................. 424/230.1

OTHER PUBLICATIONS

Alaeddine, F., et al., "Reduced Infection and Protection from Clinical Signs of Cerebral Neosporosis in C57BL/6 Mice Vaccinated With Recombinant Microneme Antigen NCMIC1", *J. Parasitol.*, 91(3), 2005, pp. 657-665.
Cannas, A., et al., "Reduced Cerebral Infection of *Neospora caninum*-Infected Mice After Vaccination With Recombinant Microneme Protein NCMIC3 and Ribi Adjuvant", *J. Prasitol.*, 89(1), 2003, pp. 44-50.
Cannas, A., et al., "Vaccination of Mice Against Experimental *Neospora caninum* Infection using NcSAG1-and NcSRS2-Based Recombinant antigens and DNA vaccines", *Parasitology*, (2003), 126, pp. 303-312.
Liddell, S., et al., "Immunization of Mice with Plasmid DNA Coding for NcGrA7 or NcsHSP33 Confers Partial Protection Against Vertical Transmission of *Neosora caninum*", *J. Parasitol.*, 89(3), 2003, pp. 496-500.
Nishikawa, Y., et al., "Delivery of *Neospora caninum* Surface Protein, NcSRS2 (Nc-p43), to Mouse Using Recombinant Vaccinia Virus", *Parisitol Res*, (2000), 86, pp. 934-939.

Nishikawa, Y., et al., "Protective Efficacy of Vaccination by Recombinant Vaccinia Virus Against *Neospora caninum* Infection", *Vaccine*, 19 (2001), pp. 1381-1390.
Nishikawa, Y., et al., "Prevention of Vertical Transmission of *Neospora caninum* in BALB/c Mice by Recombinant Vaccinia Virus Carrying NcSRS2 gene", *Vaccine*, 19 (2001), pp. 1710-1716.
Pinitkiatisakul, S., et al., "Immunisation of Mice Against Neosporisis With Recombinant NcSRS2 Iscoms", *Veterinary Parasitology*, 129, (2005), pp. 25-34.
Pinitkiatisakul, S., et al., "Immunogenicity and Protective Effect Against Murine Cerebral Neosporosis of Recombinant NcSRS2 in Different Iscom Formulations", *Vaccine*, 25, (2007), pp. 3658-3668.
Tuo, W., et al., "Identification and Characterization of *Neospora caninum* Cyclophilin That Elicits Gamma Interferon Production", *Infection and Immunity*, Aug. 2005, pp. 5093-5100.
Vemulapalli, R., et al., "Reduced Cerebral Infection of *Neospora caninum* in BALB/c Mice Vaccinated With Recombinant *Brucella abortus* RB51 Strains Expressing *N. caninum* SRS2 and GRA7 Proteins", *Veterinary Parasitology*, 148, (2007), pp. 219-230.
Zhang, H., et al., "Apical Membrane Antigen 1 is a Cross-Reactive Antigen Between *Neospora caninum* and *Toxoplasma gondii*, and the anti-NcAMA1 antibody inhibits host cell invasion by both parasites", *Molecular and Biochem. Parasitol.*, 151, (2007), pp. 205-212.
Zhang, H., et al., "Identification of Ribosomal Phosphoprotein PO of *Neospora caninum* as a Potential Common Vaccine Candidate for the Control of Both Neosporosis and Toxoplasmosis", *Molecular and Biochem. Parasitol.*, 153, (2007), pp. 141-148.

* cited by examiner

*Primary Examiner*—Larry R Helms
*Assistant Examiner*—Padma V Baskar
(74) *Attorney, Agent, or Firm*—John D. Fado; Evelyn M. Rabin

(57) ABSTRACT

*Neospora caninum* is the causal agent of bovine neosporosis which results in high levels of abortion. The protective efficacy of two *Neospora* antigens: *Neospora* cyclophilin (NcCyP) and NcSRS2 was evaluated. Mice vaccinated with recombinant (r) NcCyP, rNcSRS2, and the combination rNcCyP plus rNcSRS2, formulated with adjuvant ImmuMax-SR® and CpG were challenge-infected 3 weeks following the booster immunization and necropsied 3 weeks after the challenge infection. Mice vaccinated with rNcCyP, rNcSRS2, or the combination of rNcCyP and rNcSRS2 responded with high levels of NcCyP- or NcSRS2- specific antibodies. Mice which received vaccines formulated with either rNcCyP or the combination rNcCyP and rNcSRS2 had a higher (p<0.01) percent protection when compared to the mock- or non-vaccinated mice. Groups immunized with rNcSRS2 alone exhibited slightly lower levels of protection. Results indicate that NcCyP is a highly efficacious vaccine candidate useful in protection against *Neospora* infection.

9 Claims, 6 Drawing Sheets

A

```
NC  MKLLFFFLVLAVSAAVAENAGVQKAFMDIEIDGESAGRIVLELRGDVVPKTVKMFIGLFD   60
TG  ---VL---A----G---------R--Y----D----H----I----E-IA----------   60

NC  KYKGSTFHRVIADFMIQGGDFENHNGTGGHSIYGPRFEDENFTLKHDRGVISMANAGPNT  120
TG  -------V---I-P----------------------R---D----D---E----------  120

NC  NGSQFFITTVKTEWLDGRHVVFGKITNDSWPTVQAIEALGSSGGRPSKIAKITDIGLL    178
TG  ---------------A-----------TE----------------G-----V--------E 179
```

Fig. 1

NEOSPORA CANINUM VACCINE

BACKGROUND OF THE INVENTION

1. Field of the Invention

*Neospora caninum* is a protozoan parasite that is the causal agent of bovine neosporosis; infection results in high levels of abortion and stillbirth in cattle. This invention relates to a vaccine which comprises a recombinant *Neospora* cyclophilin protein (rNcCyP) and the method of using rNcCyP as a vaccine to protect cattle from *N. caninum* infection.

2. Description of the Relevant Art

*N. caninum* is a protozoan parasite that causes neosporosis in dogs and cattle (Dubey et al. 1989. *J. Parasitol.* 75: 146-148; Dubey et al. 2007. *Clin. Microbiol. Rev.* 20: 323-367). The only recognizable clinical manifestations of neosporosis in cows are reproductive failure such as abortion and still birth and birth of congenitally infected and clinically weak calves (Dubey, J. P. 2007. *Vet. Clin. North Am. Food Anim. Pract* 21: 473-483).

A killed whole-cell *N. caninum* tachyzoite vaccine has been tested (1) in cattle (Andrianarivo et al. 2005. *Parasitol. Res.* 96: 24-31; Andrianarivo et al. 2001. *Parasitol. Res.* 87: 817-825; Andrianarivo et al. 1999. *Int. J. Parasitol.* 29: 1613-1625; Andrianarivo et al. 2000. *Int. J. Parasitol.* 30: 985-990; Barling et al. 2003. *J. Am. Vet Med. Assoc.* 222: 624-627; Choromanski and Block. 2000. *Parasitol. Res.* 86: 851-853; Moore et al. 2005. *Vet Parasitol.* 130: 29-39; Romero et al. 2004. *Vet. Parasitol.* 123: 149-159; Williams et al. 2007. *Infect. Immun.* 75:1342-1348), (2) in mice (Liddell et al. 1999a. *J. Parasitol.* 85: 1072-1075; Miller et al. 2005. *Int. J. Parasitol.* 35: 821-828) and (3) in sheep (Jenkins et al. 2004b. *Am. J. Vet Res.* 65: 1404-1408; O'Handley et al. 2003. *Am. J. Vet. Res.* 64: 449-452); this vaccine could only achieve partial protection and was inconsistent from study to study. The currently marketed vaccine (NeoGuard) against bovine neosporosis using the whole-cell *N. caninum* tachyzoite lysate (NcAg) as antigen had a reported protection rate of approximately 50% in beef cattle (Romero et al., supra). The approach of live attenuated *N. caninum* tachyzoite vaccine was also attempted in mice and cattle (Lindsay et a. 1999. *J. Parasitol.* 85: 64-67; Miller et al., supra; Ramamoorthy et al. 2007a. *Int J. Parasitol.* 37: 1521-1529; Ritter et al. 2002. *J. Parasitol.* 88: 271-280), but its efficacies need to be further confirmed. Williams and colleagues have recently demonstrated that cows immunized with Nc Nowra, an *N. caninum* isolate that is low in virulence, were protected against fetal deaths. The whole-cell tachyzoite lysate had no effect in the Williams study and is thus a further indication that the approach of whole-cell tachyzoite lysate vaccine appears not to work (Williams et al., supra).

Concurrent with research relying on the use of whole-cell *Neospora* tachyzoite antigen, subunit vaccine research has revealed that single or multivalent subunit vaccines can result in equally effective or better protection than whole cell or lysate vaccines. In addition, they elicit specific immune responses. The subunit vaccine candidates tested so far included NcSRS2 in dogs and mice (Cannas et al. 2003a. *Parasitology* 126: 303-312; Cho et al. 2005. *Korean J. Parasitol.* 43: 19-25; Haldorson et al. 2005. *Int. J. Parasitol.* 35: 1407-1415; Nishikawa et al. 2000. *Int. J. Parasitol.* 30: 1167-1171; Nishikawa et al. 2000. *Parasitol. Res.* 86: 934-939; Nishikawa et al. 2001a. *J. Clin. Microbiol.* 39: 3987-3991; Nishikawa et al. 2001b. *Vaccine* 19: 1710-1716; Pinitkiatisakul et al. 2007. *Vaccine* 25: 3658-3668; Pinitkiatisakul et al. 2005. *Vet Parasitol.* 129: 25-34; Ramamoorthy et al. 2007b. *Int. J. Parasitol.* 37: 1531-1538; Vemulapalli et al. 2007. *Vet. Parasitol.* 148: 219-230), NcSAG1 (Cannas etal., 2003a, supra; Nishikawa et al. 2001c. *Vaccine* 19: 1381-1390; Nishikawa et al. 2001b, supra), NcMIC3 (Cannas et al., 2003b. *J. Parasitol.* 89: 44-50; Ramamoorthy et al. 2007a, b, supra), NcGRA7 (Jenkins et al. 2004a. *Infect. Immun.* 72: 1817-1819; Liddell et al. 2003. *J. Parasitol.* 89: 496-500; Vemulapalli et al., supra), NcsHSP33 (Liddell et al. 2003, supra), NcDG1 and NcDG2 (Cho et al., supra), NcMIC1 (Alaeddine et al. 2005. *J. Parasitol.* 91: 657-665; Ramamoorthy et al. 2007a, b, supra), NcAMA1 (Zhang et al. 2007a. *Mol. Biochem. Parasitol.* 151: 205-212), NcP0 (Zhang et al. 2007b. *Mol. Biochem. Parasitol.* 153: 141-148), and NcGAR2, NcGRA6 (Ramamoorthy et al. 2007a, b, supra). Of all the vaccine candidates tested so far, the most efficacious and promising subunit vaccines include those that use NcSRS2 or NcGRA7 as antigen.

Thus, although numerous studies have been attempted to develop an efficacious vaccine against bovine neosporosis, to date there are no effective chemo- or immuno-prophylactic treatments for this protozoal disease. Recent analysis of the published quantitative data indicated that vaccination might be the most economical intervention in the control of neosporosis, particularly in herds with high prevalence of *N. caninum* infection (Reichel et al. 2006. *Vet Parasitol.* 142: 23-34). This further illustrates the urgent need to develop a vaccine against neosporosis in cattle which would prevent or limit the disease.

SUMMARY OF THE INVENTION

We have discovered that recombinant *Neospora* cyclophilin protein, rNcCyP, can be used as a vaccine to protect individuals from *N. caninum* infection.

In accordance with this discovery, it is an object of the invention to provide a recombinant *Neospora* cyclophilin protein (rNcCyP) and peptides, comprising all or part of the amino acid sequence shown in SEQ ID NO:2, that can elicit an immune response specific for *N. caninum* in mammals wherein the immune response provides protection against or reduces the severity of infection caused by *N. caninum*.

Another object of the invention relates to a method of inhibiting or ameliorating a *N. caninum* infection in an individual comprising administering to an individual in need of such treatment an amount of recombinant NcCyP effective to prevent or decrease the severity of neosporosis.

The invention also relates to methods for the prevention or treatment of *N. caninum* infection in a mammal, by administration of pharmaceutical or vaccine composition of the invention, a composition comprising NcCyP together with an adjuvant, a preferred adjuvant being ImmuMax-SR®/CpG. An additional vaccine composition comprises a second antigen, NcSRS2 or recombinant NcSRS2 (rNcSRS2) in addition to NcCyP and the adjuvant ImmuMax-SR®/CpG.

It is an additional object of this invention to provide rNcCyP and peptides, and the genes which encode them, that are effective vaccines for the immunization of animals against *N. caninum* infection or neosporosis.

An added object of the invention is to provide vaccine compositions and methods useful for protecting animals against neosporosis and for decreasing the severity of *N. caninum* infection.

Another object of the invention relates to a method of protecting an individual comprising administering to an individual an amount of protein and peptides of this invention capable of eliciting from the individual a B- or T-cell immune response effective to prevent or to decrease the severity of neosporosis.

Still another object of the invention relates to methods of using NcCyP, and/or compositions thereof, to induce or elicit serum antibodies which have activity against *N. caninum*. NcCyP and/or compositions thereof are effective as vaccines to induce serum antibodies which are useful to prevent or reduce the severity of infections caused by *N. caninum*.

The invention also relates to nucleic acids encoding NcCyP of *N. caninum*, and compositions thereof, which produce NcCyP in sufficient amounts to be useful as pharmaceutical compositions or vaccines to induce serum antibodies for preventing illnesses caused by *N. caninum*. The invention also relates to suitable expression systems, viral particles, vectors, vector systems, and transformed host cells containing those nucleic acids.

The invention also relates to antibodies which immunoreact with the NcCyP of *N. caninum*, and/or compositions thereof.

The invention also relates to pharmaceutical compositions and/or vaccines comprising NcCyP, nucleic acids, viral particles, vectors, vector systems, transformed host cells or antibodies of the invention.

The invention also provides kits comprising one or more of the agents of the invention which are useful for vaccinating mammals for the treatment or prevention of *N. caninum* infection.

Further, the invention can comprise fusion proteins comprising one of the peptides described above comprising one or more epitopes of recombinant NcCyP (rNcCyP) protein wherein said rNcCyP protein comprises an amino acid sequence shown in SEQ ID NO:2 and wherein said protein is antigenic and effective to elicit an immune response against *N. caninum* in a host animal and a second unrelated peptide expressed by a regulatory DNA segment operably coupled to the DNA segment described above that encodes the peptide of this invention. In addition, the invention can comprise fusion proteins comprising the unrelated peptide expressed by a regulatory DNA segment operably coupled to a DNA nucleotide sequence encoding a fusion protein comprising one of the peptides described above comprising one or more epitopes of rNcCyP protein wherein said rNcCyP protein comprises an amino acid sequence shown in SEQ ID NO:2 and wherein said protein is antigenic and effective to elicit an immune response against *Neospora caninum* in a host animal operably coupled to yet another unrelated polypeptide sequence (different from the regulatory protein). It is part of this invention to provide the genes which encode these fusion proteins. For example, a fusion protein can comprise both NcCyP and NcSRS2 proteins or peptides or epitopes of each. The fusion protein can also comprise a polypeptide related to another disease, as for example, toxoplasmosis that is caused by *Toxoplasma gondii*.

Other objects and advantages of this invention will become readily apparent from the ensuing description.

BRIEF DESCRIPTION OF THE DRAWINGS

FIG. 1 shows the amino acid sequence comparison between NcCyP (SEQ ID NO:2) and *T. gondii* 18-kDa cyclophilin (*T. gondii* C-18; SEQ ID NO:7). NcCyP and *T. gondii* 18-kDa cyclophilins have an overall amino acid sequence homology of 86%. NcCyP protein sequence has a total of 178 amino acids with a predicted signal peptide of 17 amino acids. NcCyP is 1 amino acid shorter at the N terminus than that in *T. gondii* C-18. Dashes indicate identical amino acids between the *N. caninum* and *T. gondii* CyP sequences.

DETAILED DESCRIPTION OF THE INVENTION

Figure 2:
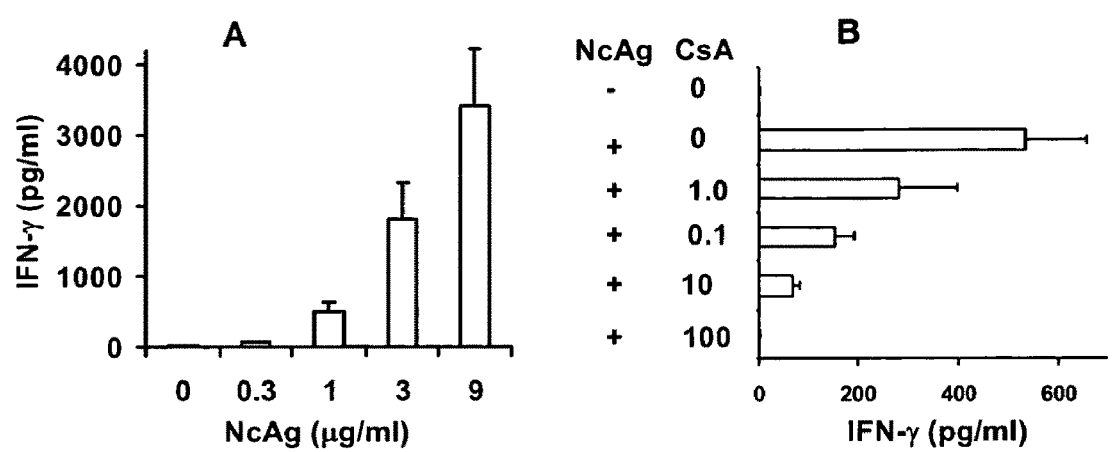
FIG. 2A depicts IFNγ production in cultured mouse splenocytes in the presence of increasing concentrations of NcAg.
FIG. 2B depicts the inhibitory effect of increasing amounts of cyclosporine A (CsA) on NcAg-induced IFNγ production in mouse splenocytes cultured for 24 hr. Data represent mean±standard error of mean from 3 separate experiments.

NcCyP is a recently identified secretory *Neospora* antigen. NcCyP has been characterized as a potent modulator of bovine host IFNγ production (Tuo et al. 2005. *Infect. Immun.* 73: 5093-5100) but has never been tested as a vaccine candidate. The purpose of using NcCyP as a vaccine candidate is that it can serve as a foreign antigen as well as an immune modulator capable of upregulating initiation cytokines such as interleukin-12 (IL-12) and IFNγ at the time of antigen priming. The ability of NcCyP to specifically induce murine IFNγ production was confirmed in mouse splenocytes in this study.

The present study determined the efficacies of vaccine candidates NcCyP and/or NcSRS2 formulated with ImmuMax-SR® and CpG in female BALB/C mice. Overall, mice vaccinated with NcCyP, NcSRS2, or the combination of both antigens had significantly higher protection against *N. caninum* tachyzoite challenge infection compared to that of mice immunized with non-recombinant control antigen. These results for the first time indicate that NcCyP is at least as efficacious as NcSRS2 in protection against *N. caninum* challenge infection in the mouse model for neosporosis. In fact, for both trials the vaccine formulated with NcCyP and ImmuMax-SR®/CpG had a percent protection of as high as 80-93%, whereas the percent protection of the vaccine containing NcSRS2 and ImmuMax-SR®/CpG was 60% for both trials. The combination of both antigens did not improve the efficacy of the vaccine, suggesting that most of the protective response is due to NcCyP.

Similar levels of specific antibodies against NcCyP or NcSRS2 were detected in mice immunized with either antigen alone or both. Antigen-specific antibody levels of vaccinated groups strongly correlated with protection conferred by vaccines formulated with either NcCyP or NcSRS2 alone or in combination. Challenge infection did result in slight increase in anti-NcSRS2 antibodies which apparently had no correlation with protection. It is presently unclear why mice immunized with vaccine containing NcCyP alone produced moderate levels of anti-NcSRS2 antibodies, or vice versa. It is possible that both native antigens are highly immunogenic, and challenge infection with *N. caninum* tachyzoites elicited a rapid response. Specific antibody levels detected by ELISA using purified recombinant *Neospora* antigens were also confirmed with Western blotting using whole-cell native *Neospora* antigens; differences in results reflect the different levels of sensitivity of ELISA and Western blot assays. It appears that NcSRS2 is more antigenic than NcCyP in that almost 100% of the mice immunized with NcSRS2 had detectable antibodies against NcSrS2, while about 77% of the mice immunized with NcCyP had detectable antibodies against NcCyP when assayed with Western blotting. However, as stated above, Western blotting is less sensitive than ELISA, therefore lower levels of anti-NcCyP antibodies can be detected by ELISA as compared to Western blotting in some individual mice. Our ELISA results clearly indicate that all mice had detectable levels of NcCyP-specific antibodies and the overall anti-NcCyP antibody levels were comparable to those of anti-NcSRS2 antibodies.

This study has also confirmed that NcCyP mediates NcAg-induced IFNγ production by mouse spleen cells, which is consistent with the effect of NcCyP on bovine immune cells and that of Toxoplasma C-18 on mouse spleen cells (Aliberti et al. 2003. *Nat. Immunol.* 4: 485-490; Tuo et al., supra). It has been speculated that CyP may play a role for a parasite such as *T. gondii* in maintaining the survival of its host, therefore, promoting its longevity of survival during evolution (Aliberti et al., supra). However, the mechanism by which pathogen-derived IFNγ-inducing proteins such as NcCyP act as a protective antigen is intriguing, given that numerous studies suggest that IFNγ is one of the most critical cytokines mediating host protection against infection by *N. caninum* and *T gondii*. So far, there is no evidence to demonstrate how CyP-induced IFNγ functions at the time of antigen priming and with other immunoregulatory effects of CyP on antigen-presenting cells and T cells. Regardless of the overall role of CyP during immune priming process, its function in enhancing IL-12 and IFNγ production was taken into consideration prior to these trials. The dual role of NcCyP as a parasite antigen as well as an initiation immunoregulatory molecule for inducing IL-12 and IFNγ can be utilized to simultaneously elicit an antigen-specific immune response to *N. caninum* and to skew the immune response towards a Th1 phenotype. Over the last few years it has been shown that CD4+ T helper cells generally fall into one of two distinct subsets, the Th1 and Th2 cells. Th1 cells principally secrete IL-2, IFNγ, IFNα, IL-12 and TNFβ; while Th2 cells principally secrete IL4, IL-5, IL-6, and IL-10. Confirmation of the presence and quantity of the Th1 response can be determined by assaying for the presence of the cytokines associated with the Th1 response, IL-2, IFNγ, IFNα, IL-12 and TNFβ, using methods known in the art, for example immunoassays such as ELISA.

To avoid a compromised recall immune response in the event of a reduced or an absence of NcCyP activity resulting from antibody-mediated neutralization, the adjuvant CpG, a proven Th1 immune response-inducer, was included in the vaccine formulation. Thus, CpG was used not only to achieve a strong biased Th1 immune response, but also to compensate for possible compromised recall immune response caused by a reduced or an absence of the immunoregulatory effect of NcCyP.

The present study demonstrates that NcCyP as a vaccine candidate is efficacious in protection against challenge infection by *N. caninum* in the mouse model.

The invention relates to rNcCyP, and/or compositions thereof, which are useful for eliciting an immunogenic response in mammals, in particular, cattle, including responses which provide protection against, or reduce the severity of, infections caused by *N. caninum*. The invention also relates to methods of using such NcCyP, and/or compositions thereof, to induce serum antibodies against NcCyP. NcCyP, and/or compositions thereof, are useful as vaccines to induce serum antibodies and to induce and to enhance IFNγ production; such results are useful to prevent or reduce the severity of infections caused by *N. caninum*. NcCyP of this invention is expected to induce a strong protective IgG antibody response in mammals, including cattle.

The invention also relates to nucleic acids encoding NcCyP and mutant forms of NcCyP of this invention and compositions thereof, as vaccines or pharmaceutical compositions to induce B cell responses, e. g., serum antibodies and T cell responses that are useful to prevent illnesses caused by *N. caninum*.

The invention also relates to antibodies which immunoreact with NcCyP of *N. caninum* that are induced by NcCyP of the invention, and/or compositions thereof.

The invention also relates to a method for the prevention or treatment of *N. caninum* infection in a mammal, by administration of compositions containing NcCyP of the invention, nucleic acids encoding NcCyP of the invention, and antibodies of the invention.

The invention also provides kits for vaccinating mammals for the prevention of *N. caninum* infection in a mammal comprising one or more of the agents of the invention.

The present invention also encompasses methods of using mixtures of NcCyP, nucleic acids, and/or antibodies of the invention, either in a single composition or in multiple compositions containing other immunogens, to form a multivalent vaccine for broad coverage against either *N. caninum* itself or a combination of *N. caninum* and one or more other pathogens, such as *Toxoplasma gondii*. *Neospora* CyP and *Toxoplasma* Cyp have homology of 86% at the amino acid level (FIG. 1); therefore, a multivalent vaccine comprising NcCyP having homology to *T. gondii*, together with known *T. gondii* epitopes can be an effective vaccine. The NcCyP vaccine or the multivalent vaccine of the invention can be administered concurrently with other vaccines, such as vaccines targeting *N. caninum* or vaccines targeting other pathogens. For example, it can be administer with Neogard or known vaccines targeting *T. gondii*. Here, for example, a vaccine composition comprising NcSRS2 antigen is provided.

Pharmaceutical compositions of this invention are capable, upon administration to an individual, of inducing serum antibodies against *N. caninum*.

The vaccines of this invention are intended for active immunization for prevention of *N. caninum* infection. The vaccines of this invention are designed to confer specific immunity against infection with *N. caninum*.

The methods of using the agents of this invention, and/or compositions thereof will be useful in increasing resistance to, preventing, and ameliorating *N. caninum* infection in mammals, in particular, in cattle and dogs.

The present invention also provides kits comprising vaccines for the prevention of *N. caninum*, containing NcCyP, nucleic acids, viral particles, vectors, vector systems, or transformed host cells or antibodies of the invention and/or compositions thereof. NcCyP, nucleic acids viral particles vectors, host cells and/or antibodies of the present invention may be isolated and purified by methods known in the art.

The vaccines of the invention are intended to be included in the immunization schedule of individuals at risk for *N. caninum* infection. Additionally, they may be used as component(s) of a multivalent vaccine for *N. caninum* and/or other pathogens.

As used herein, unless otherwise specifically noted, "NcCyP" refers to all forms of NcCyP which are useful in the compositions and/or methods of the invention, including isolated unmodified native or recombinant *N. caninum* NcCyP, or a modified form (variant) or fragment thereof, for use in vaccines. Recombinant NcCyP of the invention is identified by SEQ ID NO:2. The invention encompasses DNA sequences which encode peptides having amino acid sequences that are homologous to that of SEQ ID NO:2. "Homologous" peptides are defined herein as peptides having an amino acid sequence sufficiently duplicative of NcCyP to be antigenic and capable of eliciting antibody which specifically and selectively bind to NcCyP. DNA sequences encoding NcCyP with the amino acid sequence identified by SEQ ID NO:2 and DNA sequences which encode homologous proteins and which also hybridize to the DNA sequence identified by SEQ ID NO:1 (or its complement) under stringent conditions are particularly preferred.

Further, because of the degeneracy of the genetic code, there exists a finite set of nucleotide sequences which can code for a given amino acid sequence. It is understood that all such equivalent sequences are operable variants of the disclosed sequence, since all give rise to the same protein (i.e., the same amino acid sequence) during in vivo transcription and translation, and are hence encompassed by the instant invention.

The present invention also encompasses NcCyP variants. A "variant" of NcCyP may have an amino acid sequence that is different by one or more amino acid "substitutions". The variant may have "conservative substitutions", wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software. The term "biological activity" refers to rNcCyP having structural, regulatory or biochemical functions of the naturally occurring NcCyP. Likewise, "immunological activity" defines the capability of the natural, recombinant or synthetic NcCyP, or any oligopeptide thereof, to induce a specific immune response in appropriate animals or cells and to bind with specific antibodies. Variants and fragments of NcCyP must be able to produce an immune response in a mammal to which they are administered. The immune response is suitably protective against infection by *N. caninum* although the protective effect may be seen only after repeated applications, as would be determinable by methods known in the art. Modified NcCyP variants comprise peptides and proteins which resemble NcCyP in their ability to induce or elicit antibodies which bind to native NcCyP, but have different amino acid sequence. A preferred NcCyP variant is one having at least 80% amino acid sequence similarity to the NcCyP amino acid sequence (SEQ ID NO:2), a more preferred NcCyP variant is one having at least 90% amino acid sequence similarity to SEQ ID NO:2 and a most preferred NcCyP variant is one having at least 95% amino acid sequence similarity to SEQ ID NO:2 as defined by the algorithm, CLUSTRAL or PILEUP. Fragments are suitably peptides that contain at least one antigenic determinant or epitope of NcCyP.

The phrase "conservative substitution" also includes the use of a chemically derivatized residue in place of a non-derivatized residue. "Chemical derivative" refers to the chemical modification of a nucleic acid sequence encoding NcCyP or the encoded NcCyP wherein the subject nucleic acid or polypeptide has one or more residues chemically derivatized by reaction of a functional side group. NcCyP can be subject to various changes that provide for certain advantages in its use. For example, NcCyP with changes which increase in vitro and/or in vivo stability of NcCyP, while still retaining the desired immunogenic activity, e.g., inducing or eliciting the production of antibodies capable of binding native (or naturally-occurring) NcCyP. Preferably, the antibodies are neutralizing antibodies. Examples of such modifications would be replacement of hydrogen by an alkyl, acyl, or amino group; however, replacements are not limited to these groups. A nucleic acid derivative would encode a polypeptide which retains essential biological characteristics of natural NcCyP. Also included are those peptides which contain one or more naturally-occurring amino acid derivatives of the twenty standard amino acids, e.g., 5-hydroxylysine or ornithine may be substituted for lysine.

The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, humanized, CDR-grafted, and single chain antibodies, and the like. Fragments of immunoglobulins, including Fab, Fab', F(ab')$_2$ and F(v) fragments and fragments produced by an expression library, including phage display. See, e.g., Paul, Fundamental Immunology, Third Ed., 1993, Raven Press, New York, for antibody structure and terminology.

The phrases "specifically binds to" or "specifically immunoreactive with", when referring to an antibody or other binding moiety refers to a binding reaction which is determinative of the presence of the target analyte in the presence of a heterogeneous population of proteins and other biologics. Thus, under designated assay conditions, the specified binding moieties bind preferentially to a particular target analyte and do not bind in a significant amount to other components present in a test sample. Specific binding to a target analyte under such conditions may require a binding moiety that is selected for its specificity for a particular target analyte. A variety of immunoassay formats may be used to select antibodies specifically immunoreactive with a particular protein. For example, solid-phase ELISA immunoassays are routinely used to select monoclonal antibodies specifically immunoreactive with an analyte. See Harlow and Lane (1988) Antibodies, A Laboratory Manual, Cold Spring Harbor Publications, New York, for a description of immunoassay formats and conditions that can be used to determine specific immunoreactivity. Typically a specific or selective reaction will be at least twice background signal to noise and more typically more than 10 to 100 times background.

The term "peptide" as used herein refers to a molecular chain of amino acids with a biological activity (e.g., capable of binding antibody specific for NcCyP), and does not refer to a specific length of the product. Thus, inter alia, proteins, oligopeptides, polypeptides and fusion proteins as well as fusion peptides are included. Further, NcCyP and rNcCyP are interchangeable as reagents for detecting NcCyP-specific antibodies, for generating NcCyP-specific antibodies, and for vaccine development. Thus, inter alia, reference to NcCyP encompasses rNcCyP, and reference to rNcCyP encompasses NcCyP.

A nucleotide sequence (SEQ ID NO:1) encoding recombinant NcCyP is utilized to provide the rNcCyP of the invention. The clone (dbEST Id: 19687522, CF422590, 621 bp) was kindly provided by Dr. Sandy Clifton (Washington University School of Medicine, St. Louis, Mo. (GenBank, Accession No. CF422590). DNA sequences which are substantially homologous to the nucleotide sequence of SEQ ID NO:1 are also encompassed by the invention. As defined herein, two DNA sequences are substantially homologous when at least 85% (preferably at least 90% and most preferably 95%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al. 1989. Molecular Cloning: A Laboratory Manual, Cold Spring Harbor Laboratory, Cold Spring, N.Y., or DNA Cloning: A Practical Approach, Vol. I and II (Ed. D. N. Glover), IRL Press, Oxford, 1985. Sambrook et al. describe highly stringent conditions as a hybridization temperature 5-10° C. below the $T_m$ of a perfectly matched target and probe; thus, sequences that are "substantially homologous" would hybridize under such conditions.

The DNA sequences of the invention can be used to prepare recombinant DNA molecules by cloning in any suitable vector. A variety of vector-host combinations may be employed in practicing the present invention. Host cells may be either prokaryotic or eukaryotic, and, when the host cells are bacterial cells, they may be either gram-negative or gram-positive bacteria. In general, vectors containing nucleic acids encoding NcCyP can be utilized in any cell, either eukaryotic or prokaryotic, including mammalian cells (e.g., human (e.g., HeLa), monkey (e.g., COS), rabbit (e.g., rabbit reticulocytes), rat, hamster (e.g., CHO and baby hamster kidney cells) or mouse cells (e.g., L cells), plant cells, yeast cells, Sf9 or Sf21 insect cells (*Spodoptera frugiperda*), or bacterial cells (e.g., *E. coli*). However, bacterial vectors and host cells are preferred in the present invention.

Nucleic acids encoding the NcCyP of the invention can be introduced into a vector such as a plasmid, cosmid, phage, virus, viral particle or mini-chromosome and inserted into a host cell or organism by methods well known in the art. The vectors which can be utilized to clone and/or express these nucleic acids are the vectors which are capable of replicating and/or expressing the nucleic acids in the host cell in which the nucleic acids are desired to be replicated and/or expressed. See, e.g., F. Ausubel et al. 1992. Current Protocols in Molecular Biology, Greene Publishing Associates and Wiley-Interscience and Sambrook et al. (1989) for examples of appropriate vectors for various types of host cells. Vectors and compositions for enabling production of the peptides in vivo, i.e., in the individual to be treated or immunized, are also within the scope of this invention. Thus, while the protein may be administered to the target animal directly, it is also envisioned that the recombinant DNA containing an amino acid sequence encoding the protein could be administered to the animal as the immunizing agent. Suitable techniques for the treatment of animals with recombinant DNA are described, for example, by Tang et al. 1992. Nature 356:152-154 and Ulmer et al. 1993. Science 259:1745-1749, the contents of each of which are incorporated by reference herein. Strong promoters compatible with the host into which the gene is inserted may be used. These promoters may be inducible. The host cells containing these nucleic acids can be used to express large amounts of the protein useful in pharmaceuticals, diagnostic reagents, vaccines and therapeutics. Vectors include retroviral vectors and also include direct injection of DNA into muscle cells or other receptive cells, resulting in the efficient expression of the peptide, using the technology described, for example, in Wolff et al., 1990. *Science* 247: 1465-1468; Wolff et al. 1992. Human Molecular Genetics 1(6):363-369 and Ulmer et al. 1993. Science 259:1745-1749. See also, for example, WO 96/36366 and WO 98/34640. Still other suitable vector-host combinations that may be used in practicing the instant invention are described, for example, in U.S. Pat. No. 5,122,471, the contents of which are incorporated by reference herein.

Within each specific vector, various sites may be selected for insertion of the isolated DNA sequence. These sites are usually designated by the restriction enzyme or endonuclease that cuts them. For example, in pBR322, the Pst I site is located in the gene for penicillinase between the nucleotide triplets that code for amino acids 181 and 182 of the penicillinase protein.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

The DNA sequences of the invention may be inserted into the desired vector by known techniques. If, however, the vector is to serve as an expression vector, the vector should have a promoter, and the DNA sequence should be inserted in the vector downstream of the promoter and operationally associated therewith. While control sequences may be ligated to the coding sequence prior to insertion into the vector, preferably, the vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be.

The antigenic peptides of the invention are produced by growing host cells transformed by the expression vectors described above under conditions whereby the antigen is produced. The antigens are then isolated from the host cells. The selection of the appropriate growth conditions and recovery methods are well within the skill of the art. Host bacterial cells may be chosen that are mutated to be reduced in or free of proteases, so that the proteins produced are not degraded.

A recombinant NcCyP protein has been produced in the pET28 expression vector. Plasmid pETNcCyP was transformed into competent cell *E. coli* strain BL21 (DE3).

The peptides and proteins of this invention can be used as immunogens in vaccines for vaccination against *N. caninum*. The vaccines can be used to prevent or reduce susceptibility to disease caused by *N. caninum*. While the peptides are effective for eliciting antibody production in a variety of animals, the peptides are particularly preferred for the treatment of bovine animals.

The peptides and proteins of this invention can be formulated as univalent and multivalent vaccines. The present invention encompasses monomers of NcCyP, as well as homogeneous or heterogeneous polymers of NcCyP (e.g., concatenated, cross-linked and/or fused identical polypeptide units or concatenated, cross-linked and/or fused diverse peptide units), and mixtures of the polypeptides, polymers, and/or conjugates thereof. NcCyP can be used as produced or isolated by the methods described above. The protein can be mixed, conjugated or fused with other antigens, including B or T cell epitopes of other antigens. The present invention also encompasses NcCyP bound to a non-toxic, preferably non-host, protein carrier to form a conjugate. In addition to its utility as a primary immunogen, NcCyP can be used as a carrier protein to confer or enhance immunogenicity of other antigens.

When a haptenic peptide of NcCyP is used, (i.e., a peptide which reacts with anti-NcCyP specific antibodies, but cannot itself elicit an immune response), it can be conjugated to an immunogenic carrier molecule. For example, an oligopeptide containing one or more epitopes of NcCyP may be haptenic. Conjugation to an immunogenic carrier can render the oligopeptide immunogenic. Preferred carrier proteins for the haptenic peptides of NcCyP are tetanus toxin or toxoid, diphtheria toxin or toxoid and any mutant forms of these proteins such as $CRM_{197}$. Others include exotoxin A of Pseudomonas, heat labile toxin of *E. coli* and rotaviral particles (including rotavirus and VP6 particles). Alternatively, a fragment or epitope of the carrier protein or other immunogenic protein can be used. For example, the hapten can be coupled to a T cell epitope of a bacterial toxin. See U.S. Pat. Nos. 5,785,973 and 5,601,831, the teachings of which are incorporated herein. In addition, immunogenicity of NcCyP could be increased by conjugation of a carrier molecule, for example, dipalmityl lysine. (See Hopp, 1984. *Mol. Immunol.* 21: 13-16, incorporated herein by reference.) Carriers that fulfill these criteria are well known in the art. A polymeric carrier can be a natural or a synthetic material containing one or more functional groups, for example primary and/or secondary amino groups, azido groups, or carboxyl groups. Carriers can be water soluble or insoluble.

The peptides or proteins of this invention in monomeric or multimeric form can be incorporated into vaccines capable of inducing protective immunity against *N. caninum*. The peptides or proteins of this invention can be administered as multivalent subunit vaccines in combination with other antigens of *N. caninum*. For example, they may be administered in conjunction with other components of *N. caninum*, e.g., NcSRS2. Furthermore, it will be understood that peptides specific for a plurality of *N. caninum* antigens may be incorporated in the same vaccine composition to provide a multivalent vaccine. In addition, the vaccine composition may comprise antigens to provide immunity against other diseases in addition to neosporosis.

The conjugates can be formed by standard techniques for coupling proteinaceous materials. Fusions can be expressed from fused gene constructs prepared by recombinant DNA techniques as described. Also provided herein is a fusion protein that comprises the polypeptide of the invention in all its different antigenic forms and a second unrelated polypeptide encoded by, e.g., a DNA segment operably coupled to the DNA segment encoding the polypeptide of the invention. An example of the second unrelated polypeptide is beta-galactosidase, where the DNA segment encoding this gene product also contains regulatory sequences. However, other polypeptides may also be used, such as to provide a large protein component to increase immunogenicity. If the gene encoding the polypeptide of the invention is cloned within the beta-galactosidase gene, the two polypeptides may be expressed as a fusion protein and the amount of fusion protein produced is controlled by the regulatory sequences of the beta-galactosidase gene.

The preparation of vaccines which contain peptide sequences as active ingredients is generally well understood in the art, as exemplified by U.S. Pat. Nos.: 4,474,757; 4,493, 795; 4,608,251; 4,601,903; 4,599,231; and 4,599,230, all incorporated herein by reference. In formulating the vaccine compositions with the peptide or protein, alone or in the various combinations described, the immunogen is adjusted to an appropriate concentration and formulated with any suitable vaccine adjuvant and/or vaccine stabilizer. Typical stabilizers are, for example, sucrose, an alkali metal hydrogen phosphate salt, glutamate, serum albumin, gelatin, or casein. The stabilizer may be any one or more of the foregoing. Suitable adjuvants include, but are not limited to: surface active substances, e.g., hexadecylamine, octadecylamine, octadecyl amino acid esters, lysolecithin, dimethyl-dioctadecylammonium bromide, methoxyhexadecyl-gylcerol, and pluronic polyols; polyamines, e.g., pyran, dextran-sulfate, poly IC, carbopol; peptides, e.g., muramyl dipeptide, dimethylglycine, tuftsin; oil emulsions; and mineral gels, e.g., aluminum hydroxide, aluminum phosphate, etc. and immune stimulating complexes. The adjuvant may be, for example, alum or a composition containing a vegetable oil, isomannide monooleate and aluminum mono-stearate. The immunogen may also be incorporated into liposomes, or conjugated to polysaccharides and/or other polymers for use in a vaccine formulation. The preferred adjuvant of the invention is CpG, a proven type 1 immune response-inducer, and ImmuMax-SR®.

Also part of this invention is a composition that comprises the peptide of this invention; and a carrier, preferably a physiologically and/or pharmaceutically tolerable (acceptable) carrier. Typical carriers are aqueous carriers such as water, buffered aqueous solutions, aqueous alcoholic mixtures, and the like. Compositions comprising carriers that are for pharmaceutical use, particularly for use in mammals, comprise a carrier that is pharmaceutically-acceptable. Depending on the intended mode of administration, the compounds of the present invention can be in various pharmaceutical compositions. The compositions will include, as noted above, an effective amount of the selected immunogen and/or antibody of the invention in combination with a pharmaceutically acceptable carrier and, in addition, may include other medicinal agents, pharmaceutical agents, carriers, adjuvants, diluents, excipients, etc. By "pharmaceutically acceptable" is meant a material that is not biologically or otherwise undesirable, i.e., the material may be administered to an individual along with the immunogen and/or antibody or other composition without causing any undesirable biological effects or interacting in a deleterious manner with any of the other components of the pharmaceutical composition in which it is contained. Examples of such carriers are known in the art and need therefore not be provided herein.

Typically, such vaccines are prepared as injectables: either as liquid solutions or suspensions, solid forms suitable for solution in, or suspension in, liquid prior to injection may also be prepared. The NcCyP protein preparation could also be emulsified. The peptides may be administered to a target animal by any convenient route, such as subcutaneously, intraperitoneally, intramuscularly, intradermally, intravenously, orally, intranasally, or preferably intramammarily, in the presence of a physiologically acceptable diluent. The antigens may be administered in a single dose or in a plurality of doses. The antigens of the present invention may be stored under refrigeration or in frozen or lyophilized form. The proteins are administered to the target animal in an amount effective to elicit a protective immune response against *N. caninum*, as compared to a control. The effective amount will vary with the particular target animal, its age and size, and may be readily determined by the practitioner skilled in the art. Suitable regimes for initial administration and booster shots will also be variable, but may be typified by an initial administration followed by subsequent inoculations or other administrations.

The pharmaceutical compositions of this invention contain a pharmaceutically and/or therapeutically effective amount of NcCyP, nucleic acid, vector, viral particle, host cell immunogen or antibody of the invention. The effective amount of immunogen per unit dose is an amount sufficient to induce an immune response which is sufficient to prevent or protect against the adverse effects of infection with *N. caninum*. The effective amount of immunogen per unit dose depends, among other things, on the species of mammal inoculated, the body weight of the mammal and the chosen inoculation regimen, as is well known in the art.

To monitor the antibody response of individuals administered the compositions of the invention, antibody levels may be determined. In most instances it will be sufficient to assess the antibody titer in serum or plasma obtained from such an individual. Decisions as to whether to administer booster inoculations or to change the amount of the composition administered to the individual may be at least partially based on the level. The level may be based on either an immunobinding assay which measures the concentration of antibodies in the serum which bind to a specific antigen, i.e. NcCyP.

An antibody of the present invention in one embodiment is characterized as comprising antibody molecules that immunoreact with *N. caninum* NcCyP. An antibody of the present invention is typically produced by immunizing a mammal with an immunogen or vaccine containing an *N. caninum* NcCyP to induce, in the mammal, antibody molecules having immunospecificity for the immunizing NcCyP.

The antibody of the present invention may be contained in blood plasma, serum, hybridoma supernatants and the like. Alternatively, the antibodies of the present invention are isolated to the extent desired by well-known techniques such as, for example, ion exchange chromatography, sizing chromatography, or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibodies of the IgG class are preferred for purposes of passive protection. The antibodies can be measured in standard immunoassay protocols. Such assays include, but are not limited to, agglutination assays, radioimmunoassays, enzyme-linked immunosorbent assays, fluorescence assays, Western blots and the like. The antibodies of the present invention are also useful in prevention of infections and diseases caused by *N. caninum*.

The administration of the agents of the invention are for "prophylactic" purposes. When provided prophylactically, the agents are provided in advance of any symptom. The prophylactic administration of the agent serves to prevent or ameliorate any subsequent infection. The agent of the present invention may, thus, be provided prior to the anticipated exposure to *N. caninum*, so as to attenuate the anticipated severity, duration or extent of an infection and disease symptoms For all prophylactic uses, the NcCyP or other agents of this invention, as well as antibodies and other necessary reagents and appropriate devices and accessories, may be provided in kit form so as to be readily available and easily used.

Statistics: Serum antibody and cytokine levels were analyzed by one-way ANOVA with a multiple comparisons test (GraphPad, Version 3.06). Percent protection among different groups was analyzed by two-sided Fisher's Exact test (GraphPad Instat, Version 3.06). Statistical significance was considered if $P \leq 0.05$.

EXAMPLES

Having now generally described this invention, the same will be better understood by reference to certain specific examples, which are included herein only to further illustrate the invention and are not intended to limit the scope of the invention as defined by the claims.

Example 1

*N. Caninum* Tachyzoite and *N. Caninum* Whole Cell Tachyzoite Lysate Preparation

*N. caninum* tachyzoites and *N. caninum* whole cell tachyzoite lysate (NcAg) were prepared as described elsewhere (Tuo et al., supra). Briefly, *N. caninum* (NC1 isolate) tachyzoites were cultured on the African green monkey kidney cells (CV1, ATCC CCL-70) in RPMI 1640 medium supplemented with 2% fetal calf serum and 50 µg/ml gentamicin at 37° C. in a 95% air and 5% CO2 atmosphere. *N. caninum* tachyzoite-infected host cells were collected, passed through 20- and 27-gauge needles, and pelleted by centrifugation at 1,000 g for 20 min at 4° C. Tachyzoites were then purified by centrifugation over a 40% Percoll gradient at 2,000 g for 30 min at 4° C. To prepare live tachyzoites for challenge infection, the purified tachyzoite pellet was washed once in RPMI 1640, the suspension was adjusted to appropriate concentrations and placed on ice until use. To prepare NcAg, the tachyzoite pellet was resuspended in PBS (pH 7.4) and washed three times. The resulting pellet was resuspended in 25 mM Tris (pH 8.0) and subjected to three 15 s pulses of sonication on ice at maximal frequency using a sonicator (Virsonic Cell Disrupter; The Virtis Company, New York, N.Y.) in the presence of a protease inhibitor cocktail mixture (Boehringer Mannheim Cooperation, Indianapolis, Ind.). The tachyzoite cell lysate was stored at −25° C. until use. Protein concentration was determined with the bicinchoninic acid protein assay kit (BCA, Pierce, Rockford, Ill.).

Example 2

NcAg-Induced IFNγ Production in Mouse Splenocytes

Mice were euthanized by $CO_2$ and cervical dislocation. Spleens were aseptically collected and splenocytes prepared. Briefly, the spleen was forced through a metal mesh in RPMI 1640 with a syringe plunger and the cell suspension was pipeted up and down to break up cell clumps prior to isolation using Histopaque-1077 (Sigma). Isolated splenocytes were washed, enumerated and adjusted to 5×10⁶ cells per ml in complete medium. Cells (10⁶) were then added to each well of the 24 well plates and treated with increasing concentrations of NcAg (0, 0.3, 3, or 9 µg/ml) or CsA (0, 1, 10, or 100 nM) in a total volume of 2 ml RPMI 1640 medium supplemented with 10% fetal calf serum and 50 ug/ml getamicin (complete medium). Plates were incubated at 37° C. with a 5% $CO_2$ and 95% air atmosphere for 48 hr. Supernatant was collected, centrifuged and stored at −20° C. until assayed.

IFNγ production by splenocytes was highly stimulated by NcAg in a dose dependent manner (FIG. 2), which is consistent with the observation in bovine peripheral blood mononuclear cells (PBMC). As shown, low levels of NcAg were sufficient to induce high levels of INFγ production. NcAg at 1 µg/ml was used in the subsequent experiment because it induced an appreciable amount of IFNγ which could be conveniently quantified with the ELISA without further dilution. In the presence of constant amount of NcAg (1 µg/ml) and increasing concentrations of cyclosporin A (CsA), a specific inhibitor of cyclophilin, NcAg-stimulated IFNγ production was specifically inhibited in a dose-dependent fashion. CsA at a dose of 10-100 nM was effective in suppressing NcAg-elicited IFNγ production, which is also consistent with its effect in bovine PBMC (Tuo et al., supra).

A capture IFNγ ELISA with the mouse IFNγ-specific mAb (clone XMG1.2; BD Pharmagen) as the capture antibody and the rabbit antiserum to mouse IFNγ (R&D) as the detection antibody was used. The plates were pre-coated with the capture mAb and stored at −20° C. prior to use. Diluted samples or IFNγ standard (0, 1.0, 3.9, 15.6, 62.5, 250, 1000 pg) (R&G) in 100 ul per well and rabbit antiserum against IFNγ in 25 ul per well were added to the plates and incubated at room temperature overnight. Following washing, 50 µl goat anti-rabbit IgG antibody conjugated with alkaline phosphatase (KPL, Gaithersburg, Md.) was added and incubated at room temperature for 1 hr. Plates were then washed and 100 µl per well pNPP substrate (Sigma) was added, incubated at room temperature for 2 hr and read at 405 nm using an ELISA plate reader.

Example 3

Preparation of Recombinant NcCyP and NcSRS2

Nine EST clones of the NcCyP gene are found in Genbank. Only partial sequences are available for eight of the NcCyP clones; the partial sequences of all eight clones are identical. Only clone CF422590 has the full length coding region (Tuo et al., supra). This clone (dbEST Id: 19687522, CF422590, 621 bp) was kindly provided by Dr. Sandy Clifton (Washington University School of Medicine, St. Louis, Mo.) and used as the DNA template for PCR amplification and cloning. The open reading frame (ORF) encoding N. caninum cyclophilin (NcCyP) was polymerase chain reaction (PCR)-amplified and cloned into the expression vector pET28 (Novagen, Madison Wis.). In order to facilitate the cloning and downstream recombinant protein purification processes, recognition sites for restriction enzymes NdeI (CATATG) and EcoRI (GAATTC) were incorporated into the forward (5'-GCATAT-GMGCTCCTGTTC TTCTTCCTC-3'; SEQ ID NO:3) and reverse (5'-AGMTTCTTACAACAAACCM TGTCCGTGA-3'; SEQ ID NO:4) primers, respectively. The full-length NcSRS2 sequence (GenBank Accession No. NCU93870) was kindly provided by Andrew Hemphill. A 965 nt segment (nt 454-1419) of the NcSRS2 coding region without the N-terminal signal sequence or the C-terminal GPI anchor was amplified using a forward primer (5'-CCATATGGCGCCGT- TCAAGTCGGAAAAT-3'; SEQ ID NO:5) containing an NdeI recognition site and a reverse primer (5'-AGMTTCT-CATCCTCTTMCACGGGG GAATC-3'; SEQ ID NO:6) containing an EcoRI recognition site. The amplicon was initially cloned into the TOPO TA cloning vector pCRII-TOPO (Invitrogen, Carlsbad Calif.) and the insert was subsequently excised with NdeI and EcoRI double digestion and cloned into pET28 at the NdeI/EcoRI sites. In the resultant plasmid, pETNcCyP or pETNcSRS2, the NcCyP or NcSRS2 ORF was fused in-frame with an oligohistidine domain (6×His) followed by a thrombin protease cleavage site, a configuration allowing rapid metal-chelate affinity purification of the fusion protein. For production of recombinant NcCyP, plasmid. pETNcCyP was transformed into competent cell E. coli strain BL21(DE3). Single colonies from transformed BL21(DE3) cells were cultured in LB liquid medium containing 50 µg/mL kanamycin at 37° C. Recombinant protein production was induced by addition of IPTG (final concentration 1 mM) to cultures at mid-log phase (O.D$_{600}$≈0.6). Bacterial cells, harvested 1.5 hr post-induction, were treated with lysozyme (100 µg/mL) and Triton-X 100 (0.2%) for 15 min followed by brief sonication. The majority of rNcCyP and rNcSRS2 recombinant protein was present in the urea-soluble fraction of the extraction procedure. Both rNcCyP and rNcSRS2 were purified by NiNTA-affinity chromatography using procedures supplied by the manufacturer (Qiagen). The concentration of NiNTA-purified rNcCyP and rNcSRS2 proteins was estimated by BCA assay (Pierce Chemical Co.).

Figure 3:
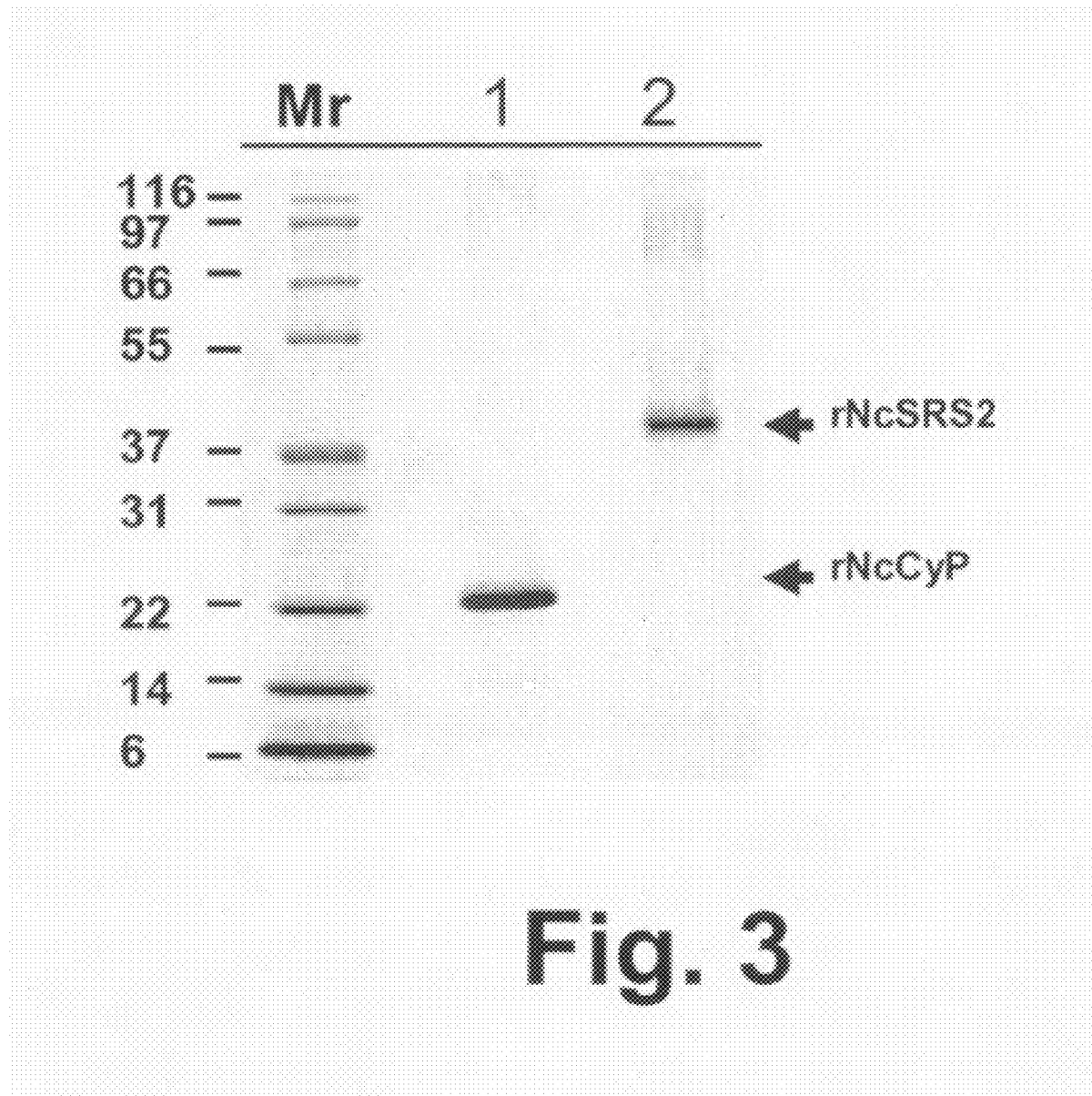
FIG. 3 shows purified recombinant NcCyP (rNcCyP) and NcSRS2 (rNcSRS2). Purified recombinant proteins were analyzed by 4-20% Tris glycine SDS PAGE under non-reducing conditions, followed by Coomassie blue staining. Molecular weight markers are indicated on the left. Lane 1, rNcCyP at 2 ug/lane; lane 2, rNcSRS2 at 2 ug/lane.

Both rNcCyP and rNcSRS2 proteins were purified from the E. coli cell lysate using a NiNTA affinity column and analyzed by SDS-PAGE (FIG. 3). The bacterial host cell protein impurities in both recombinant protein preparations were estimated 1.0-1.9% of total protein by the host cell protein assay. The monomeric band of both recombinant proteins was estimated 90.3-98.5% of total purified protein (Zhu et al. 2005. J. Immunol. Methods 306: 40-50). The non-recombinant protein (NR) similarly prepared by the nickel affinity column from the E. coli host cell lysate was used as a control antigen and contained a comparable amount of bacterial proteins when compared to purified rNcCyP and rNc-SRS2.

Example 4

Animals and Immunization Procedures

Adult female BALB/c mice (10-12 weeks old; 15 per group; National Cancer Institute, Frederick, Md.) were immunized s.c. in the lower back with a dose of 20 µg of rNcCyP, rNcSRS2, or 20 µg each of NcCyP and NcSRS2 formulated with adjuvants ImmuMax-SR® (a chitosan-based oil emulsion formulation [U.S. Pat. No. 5,980,912; Nov. 9, 1999]; (Repros Therapeutics Inc., formerly Zonagen Inc., TX) and CpG (ImmunoEasy, Qiagen) (Groups 1, 2, and 3). Control groups received non-recombinant antigen formulated with adjuvants ImmuMax-SR® and CpG (Group 4) or RPMI 1640 alone (Groups 5 and 6). The mice were given a secondary immunization 3 weeks later with the same preparation used in the primary immunization. All mice except for those in Group 6 were challenged s.c. with 10⁵ N. caninum tachyzoites (NC1 isolate) in 50 µl RPMI 1640 three weeks following the secondary immunization. Group 6 mice received RPMI 1640 only and remained uninfected throughout the experiment (Table 1). All mice were euthanized 3 weeks after challenge infection, and brain tissue and blood were collected at necropsy and processed for Neospora DNA and serum antibody analysis as described (Liddell et al.

1999b. *Int J. Parasitol.* 29: 1583-1587). Animal use and care of the present study was approved by the BARC Animal Use and Care Committee in accordance with appropriate regulations.

TABLE 1

Experimental Design Vaccine Formulation

| Group No. | Mice/Group | Neospora antigen[1] | Adjuvant[2] | Challenge[3] |
|---|---|---|---|---|
| 1 | 15 | rNcCyP | ImmuMax-SR ® + CpG | + |
| 2 | 15 | rNcSRS2 | ImmuMax-SR ® + CpG | + |
| 3 | 15 | rNcCyP + rNcSRS2 | ImmuMax-SR ® + CpG | + |
| 4 | 15 | NR | ImmuMax-SR ® + CpG | + |
| 5 | 15 | — | — | + |
| 6 | 15 | — | — | − |

[1]Antigens used were expressed in a bacterial expression system and purified by a nickel affinity column; NR, non-recombinant bacterial host cell protein purified using the same conditions to purify recombinant proteins.
[2]Adjuvants: ImmuMax-SR ® and CpG containing oligonucleotides were purchased from Repro Therapeutics Inc. (formerly Zonagen Inc.), TX and Qiagen, Inc., MD, respectively and formulated with antigens prior to use.
[3]Challenge: each mouse was inoculated s.c. with $10^5$ live *N. caninum* tachyzoites in 50 ul RPMI 1640.

Example 5

ELISA and Western Blot Analysis of NcCyP-specific Antibodies

Antigen-specific antibody levels of vaccinated mice were determined by ELISA using purified rNcCyP or rNcSRS2. Individual serum from all mice in each treatment group was assayed for antibodies to native *N. caninum* protein using ELISA. In brief, ELISA microtiter plates (ImmulonII HB, Costar) were coated with soluble *N. caninum* tachyzoite protein equivalent to $10^5$ tachyzoites/well in carbonate buffer (pH 9.5) for 1 hr at 37° C. followed by overnight incubation at 4° C. Unbound *N. caninum* tachyzoite protein was removed by washing wells with PBS. The wells were then treated with blocking reagent (PBS-2% BSA) for 1 hr at RT, followed by incubation with 1:100 dilution of individual mouse serum in duplicate for 2 hr at RT. The wells were incubated with alkaline phosphatase-labeled goat anti-mouse IgG (H+L ch. sp., 1:5,000, Sigma) for 1 hr at RT, followed by addition of p-nitrophenyl phosphate substrate (Sigma), and reading on a microtiter plate reader at 450 nm.

For both trials, mice vaccinated with rNcCyP (Group 1) or rNcCyP+rNcSRS2 (Group 3) had significantly higher ($p<0.01$) levels of NcCyP-specific antibodies when compared to mice vaccinated with rNcSRS2 alone (Group 2), vaccine control (NR) (Group 4), challenge infection only (Group 5), or those from the unvaccinated/unchallenged group (Group 6). Likewise, mice vaccinated with rNcSRS2 (Group 1) or rNcCyP+rNcSRS2 (Group 3) had significantly higher ($p<0.01$) levels of NcSRS2-specific antibodies when compared to mice vaccinated with NcCyP alone (Group 2), vaccine control (NR) (Group 4), challenge infection control (Group 5), or those from the unvaccinated/unchallenged group (Group 6). Antigen-specific antibody levels of mice vaccinated with either NcCyP or NcSRS2 did not differ ($p>0.05$) from those received NcCyP and NcSRS2 in combination.

Figure 4:
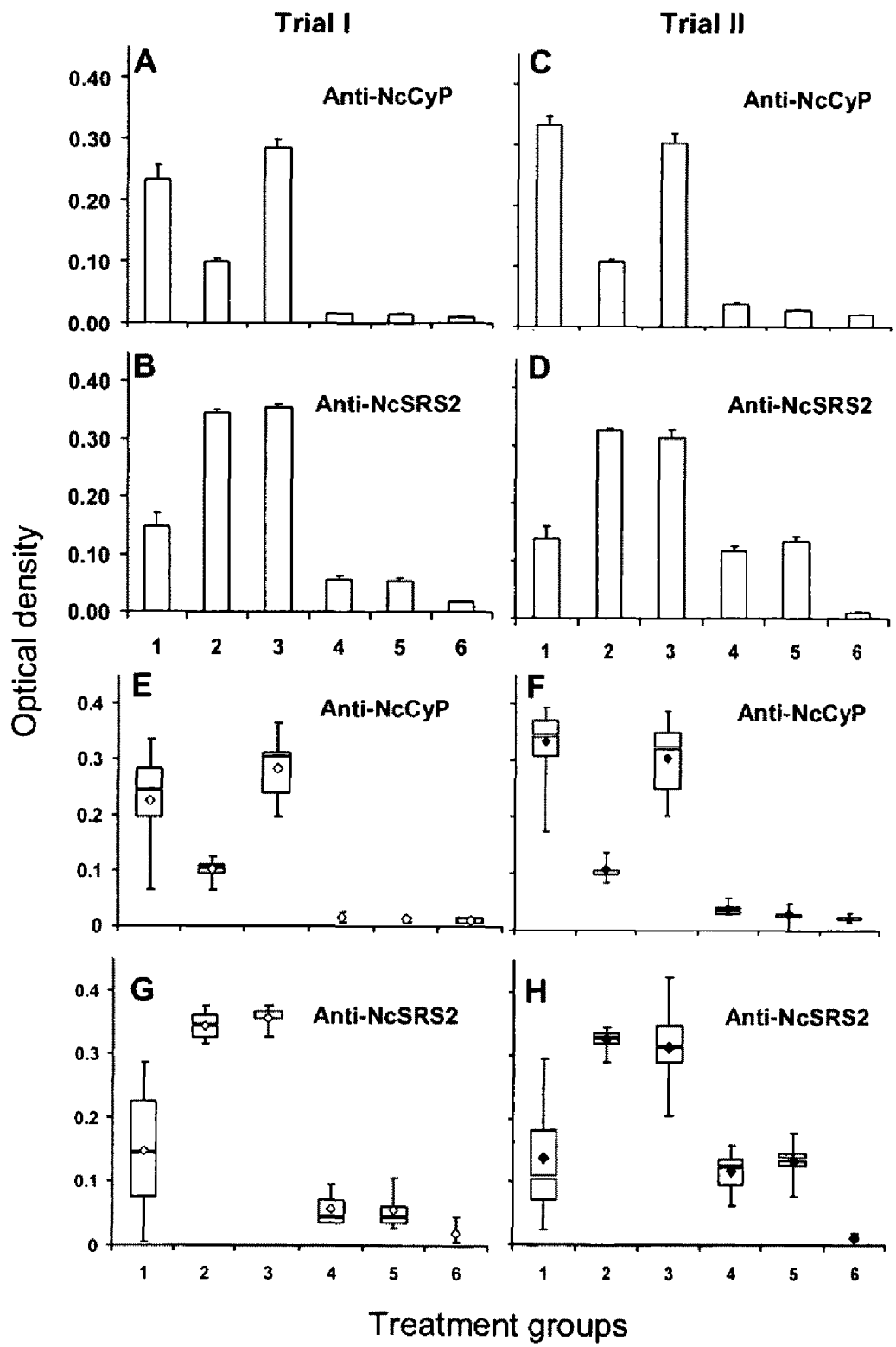
FIGS. 4A-H show the NcCyP- and NcSRS2-specific antibody levels in mouse sera determined by ELISA. Panels A and B represent antibody levels of NcCyP and NcSRS2 for Trial I and panels C and D represent antibody levels of NcCyP and NcSRS2 for Trial II. The arbitrary levels of antibodies specific for both recombinant proteins are expressed in optical density. The levels of specific antibodies to NcCyP or NcSRS2 in vaccinated groups are significantly higher ($p<0.01$) than those of non-vaccinated groups. A bar graph using mean±standard error of mean (A, B, C and D) and a box plot (E, F, G and H) are shown, where the same data are used by A and E, B and G, C and F or D and H.

A challenge infection with $10^5$ *N. caninum* tachyzoites resulted in an increase ($p<0.05$) in levels of antibodies to NcSRS2 as shown in Groups 4 and 5 (FIG. 4), however, these NcSRS2 antibody levels were significantly lower ($p<0.05$) than those of groups vaccinated with either NcSRS2 alone or both NcCyP and NcSRS2. When compared to the mock- (Group 5) and non-vaccinated (Group 6) mice, anti-NcCyP antibody levels in trials I and II increased ($p<0.05$) significantly in group 2 mice that received vaccine with NcSRS2 alone. Similarly, anti-NcSRS2 antibody levels were also higher ($p<0.05$) in Group-1 mice vaccinated with NcCyP alone than in Group 4 and 5 (control groups) mice in trial I. Nevertheless, these antibody levels are significantly lower ($p<0.001$) than those that detected with the immunizing antigens.

Figure 5:
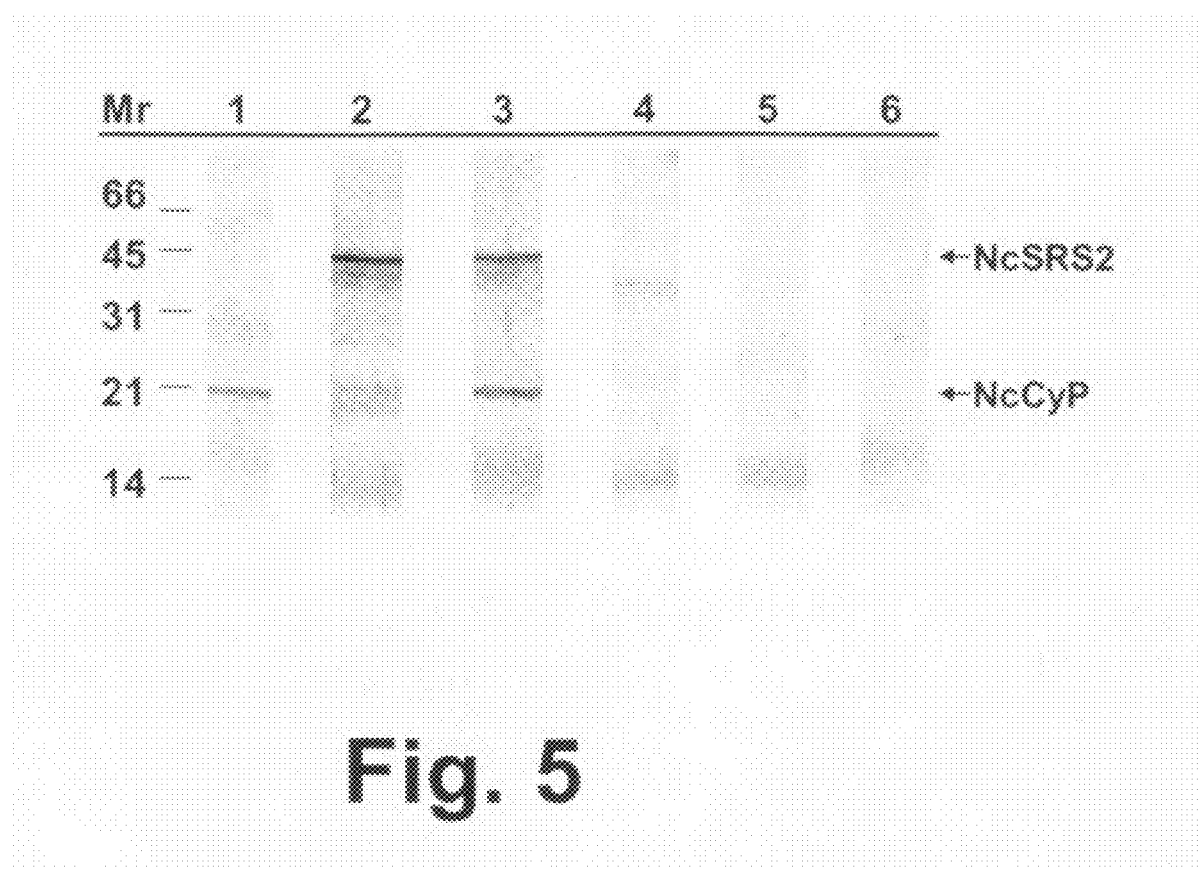
FIG. 5 shows the Western blot analysis of the serological response to native NcCyP and/or NcSRS2 proteins elicited by immunization of mice with rNcCyP (group 1), rNcSRS2 (group 2), or both rNcCyP and rNcSRS2 (group 3) proteins. Results are derived from pooled sera in each group. Lane 1, mice immunized with rNcCyP; lane 2, mice immunized with rNcSRS2; lane 3, mice immunized with rNcCyP and rNcSRS2; lane 4, mice immunized with non-recombinant protein; lanes 5 and 6, non-vaccinated mice. Mr, molecular weight markers.

The presence of specific antibodies to NcCyP or NcSRS2 was also confirmed with Western blotting using NcAg as antigen (FIG. 5). In brief, *N. caninum* tachyzoite protein (equivalent to $10^6$ tachyzoites/blot strip) were fractionated by SDS-PAGE under reducing conditions and transblotted to Immobilon membrane (Millipore) in a semi-dry blot apparatus (BioRad). Low-range molecular weight markers (Bio-Rad) were electrophoresed in a separate well to allow for Mr estimation of native *N. caninum* tachyzoite protein. After blotting, the membranes were cut into vertical strips, treated with blocking agent (PBS-2% non-fat dry milk) for 30 min at RT, and then incubated for 2 hr at RT with a 1:100 dilution of serum from individual mice in each treatment group. The blot strips were then incubated for 1 hr with biotinylated goat anti-mouse IgG (H+L ch. sp., 1:1000 dilution, Sigma Chemical Co.), followed by alkaline-phosphatase-labeled avidin (1:25,000 dilution, Sigma), and developed with NBT-BCIP substrate (Pierce). The blots were washed 3 times between each incubation step with PBS-0.05% Tween 20 (Sigma).

Overall data from both trials indicate that 78% (11.5/14.8) of the mice vaccinated with rNcCyP had detectable antibodies against NcCyP; while 100% (15/15) of the mice vaccinated with rNcSrS2 had detectable antibodies against NcSRS2. For the group (Group 3) that was vaccinated with both antigens, 77% had detectable antibodies to NcCyP and 98% had detectable antibodies to NcSRS2. No antibodies to NcCyP or NcSRS2 were detected in sera of mice vaccinated with non-recombinant control protein (Group 4) or non-vaccinated mice (Groups 5 and 6) (Table 2).

TABLE 2

Detection of anti-NcCyP or NcSRS2 antibodies in mouse sera by Western blot[1]

| | Trial I | | Trial II | |
|---|---|---|---|---|
| Group No. | NcCyP[2] | NcSRS2 | NcCyP | NcSRS2 |
| 1 | 11/14[3] | 0/14 | 12/15 | 0/15 |
| 2 | 0/14 | 15/15 | 0/15 | 15/15 |
| 3 | 12/15 | 15/15 | 11/15 | 14/15 |
| 4 | 0/15 | 0/15 | 0/15 | 0/15 |
| 5 | 0/15 | 0/15 | 0/15 | 0/15 |
| 6 | 0/15 | 0/15 | 0/15 | 0/15 |

[1]Whole-cell *N. caninum* tachyzoite lysate (NcAg) was used as antigen in Western blotting.
[2]Mouse sera from these studies were used as primary antibodies, and goat anti-mouse IgG conjugated to alkaline phosphatase was used secondary antibody.
[3]Data represent number of mice with detectable anti-NcCyP or anti-NcSRS2 Ab in total mice of the group.

Example 6

*N. Caninum* DNA Sequence-specific PCR

Mouse brain tissue was extracted for DNA using standard procedures (Jenkins et al. 2004, supra). The presence of *N. caninum* in brain tissue was determined by *N. caninum*-specific Nc5 PCR using Np6/Np21 primers (Muller et al. 1996. *J.*

Clin. Microbiol. 34: 2850-2852; Yamage et al. 1996. *J. Parasitol.* 82: 272-279) and an internal standard to control for false negative reactions as described (Jenkins et al. 2004a, supra; Liddell et al. 1999a, supra).

The presence of *N. caninum*-specific DNA sequences in brains of BALB/c mice with or without vaccination against *N. caninum* and its relation to protection against *N. caninum* infection was determined. In both trials, 80-100% of mice in the non-vaccinated challenge infection control group (Group 5) and 73-93% of mice in the non-recombinant protein-vaccinated group (Group 4) displayed detectable levels of *N. caninum* in brain tissue (Table 3).

TABLE 3

Detection of *N. caninum* DNA sequence in brains of female BALB/c mice with or without vaccination against *N. caninum* infection.

| Group Number | Trial I Positive/Total[1] | Trial II Positive/Total | Positive/Total (Mean)[2] |
|---|---|---|---|
| 1 | 1/15 | 3/15 | 2/15 |
| 2 | 6/15 | 6/15 | 6/15 |
| 3 | 5/15 | 1/15 | 3/15 |
| 4 | 11/15 | 13/14 | 12/14.5 |
| 5 | 12/15 | 15/15 | 13/15 |
| 6 | 0/15 | 0/13 | 0/14 |

[1]Positive/total = number of mice brain positive for *N. caninum* DNA/total mice in the group.
[2]Mean positive/total from trials I and II.

Figure 6:
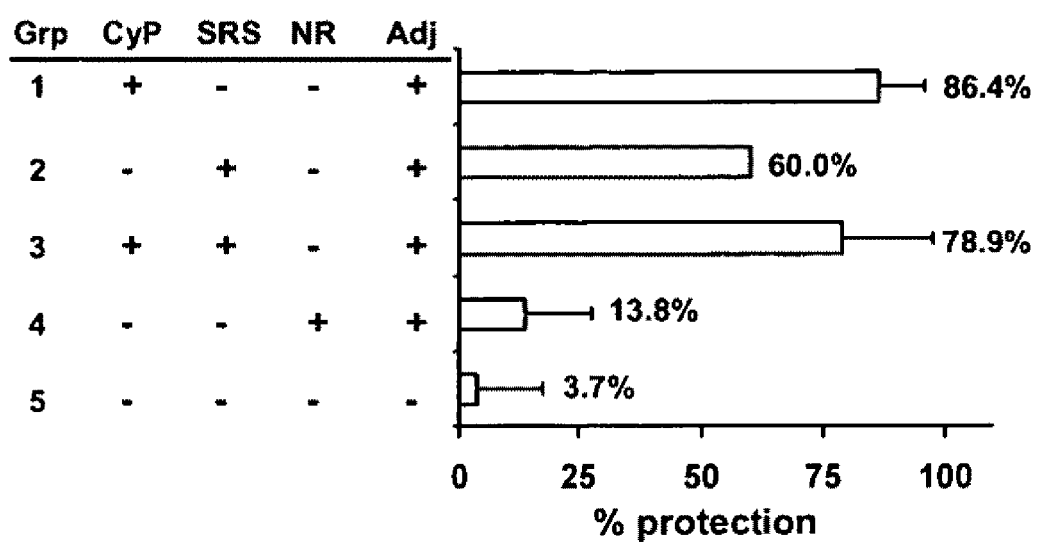
FIG. 6 depicts the percent protection of vaccinated and non-vaccinated mice. Data represent geometric means with standard deviation of percent protection from two trials. Grp, group number; CyP, rNcCyP; SRS, rNcSRS2; NR, non-recombinant antigen; Adj, adjuvants, ImmuMax-SR®/CpG. Percent protection=(number of mice brain negative for Nc DNA/total number of mice in the group)×100.

Levels of protection among groups vaccinated with rNcCyP, rNcSRS2, or both rNcCyP and rNcSRS2 did not significantly differ (p>0.05). The groups (Group 1) vaccinated with rNcCyP alone had an average of 13% (7-20%) mice brain-positive for *N. caninum* and showed higher (p<0.001) levels of protection when compared to the non-recombinant or non-vaccinated groups. In comparison to non-recombinant- or non-vaccinated groups, significantly higher (p<0.01) protection was also observed in groups (Group 3) immunized with a combination of NcCyP and NcSRS2 with an average of 20% (7-33%) *N. caninum*-positive mice. The groups (Group 2) immunized with rNcSRS2 alone, with an average of 40% mice brain-positive for *N. caninum*, exhibited slightly lower levels of protection which was higher (p<0.05) than that of the non-vaccinated group but did not differ (p=0.06) from that of the non-recombinant-vaccinated group (Table 3, FIG. 6). Immunization with vaccines containing NcCyP resulted in higher percent protection than vaccine with NcSRS2 alone (78.9-86.4% vs. 60% in protection), but it was not statistically significant.

Overall, high levels of protections were attained when mice were immunized with vaccines containing rNcCyP when compared to controls. *N. caninum* DNA was not detectable in the brain of the mice from the uninfected control group (Group 6) for both trials indicating negligible contamination of brain tissue by *N. caninum* DNA (Table 3).

Thus, overall, mice vaccinated with NcCyP, NcSRS2, or the combination of both antigens had significantly higher protection against *N. caninum* tachyzoite challenge infection compared to that of mice immunized with non-recombinant control antigen. These results for the first time indicate that NcCyP is at least as efficacious as NcSRS2 in protection against *N. caninum* challenge infection in the mouse model for neosporosis. In fact, for both trials, the vaccine formulated with NcCyP and ImmuMax-SR®/CpG had a percent protection of as high as 80-93%, whereas the percent protection of the vaccine containing NcSRS2 and ImmuMax-SR®/CpG was 60% for both trials.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A vaccine comprising an effective amount of an isolated or recombinant *Neospora caninum* cyclophilin protein (rNc-CyP) consisting of the amino acid sequence set forth in SEQ ID NO: 2, an adjuvant and a pharmaceutically acceptable carrier, wherein the adjuvant is a Zinc-Chitosan and CpG, wherein the vaccine protects animals against *N. caninum* infection and neosporosis.

2. The vaccine of claim 1 wherein said vaccine in addition comprises one or more additional isolated or recombinant *N. caninum* proteins or epitopes.

3. The vaccine composition of claim 2, wherein said one additional isolated or recombinant *N. caninum* protein is a tachyzoite surface protein (NcSRS2).

4. The vaccine of claim 1, wherein said vaccine in addition comprises one or more additional isolated or recombinant proteins or epitopes from at least one organism pathogenic for cattle and dogs and said pathogenic organism is different from *N. caninum*.

5. The vaccine composition of claim 4, wherein said additional isolated or recombinant protein or epitope is from *Toxoplasma gondii*.

6. The vaccine of claim 1 which stimulates in a mammalian host a *N. caninum*-specific antibody response and a cell-mediated immune response.

7. The vaccine of claim 6 wherein said cell-mediated immune response is a Th1 immune response and results in the induction of IFNγ production.

8. A method for protecting an animal against *N. caninum* infection and neosporosis comprising administering to said individual the vaccine of any one of claims 1 or 2-7 in an amount effective to protect said animal from clinical neosporosis.

9. A method for protecting an animal against *N. caninum* infection and neosporosis comprising administering to said individual the vaccine of any one of claim 1 and or 2-7 in an amount effective to elicit an immune response against *N. caninum* therein, wherein said immune response is a *N. caninum*-specific antibody response and a *N. caninum*-induced cell-mediated immune response resulting in the Induction of IFNγ production.

* * * * *

SEQUENCE LISTING

<160> NUMBER OF SEQ ID NOS: 7

<210> SEQ ID NO 1
<211> LENGTH: 537
<212> TYPE: DNA
<213> ORGANISM: Neospora caninum

<400> SEQUENCE: 1

```
atgaagctcc tgttcttctt cctcgttctt gcggtttctg ccgccgtagc ggaaaacgcc      60
ggagtccaga aggcattcat ggatatcgaa attgacggtg aaagcgctgg acgcattgtg     120
ctggagctcc gtggcgacgt ggtccctaag actgtgaaga acttcattgg tctcttcgac     180
aagtacaaag gcagcacgtt ccaccgcgtc atcgccgact tcatgatcca gggaggagac     240
ttcgagaacc acaacggaac cggaggacac agcatatatg gccccagatt cgaagacgag     300
aacttcacgt tgaagcacga cagaggtgtc atctcaatgg caaatgctgg cccgaacacg     360
aacggcagtc agttcttcat cacaacggtg aagacagagt ggctggacgg cagacacgtt     420
gttttcggaa aaatcacgaa cgactcttgg cccaccgtcc aggccattga ggcgctcggc     480
agcagcggcg gccgcccctc caagatcgcg aagatcacgg acattggttt gttgtaa       537
```

<210> SEQ ID NO 2
<211> LENGTH: 178
<212> TYPE: PRT
<213> ORGANISM: Neospora caninum

<400> SEQUENCE: 2

Met Lys Leu Leu Phe Phe Phe Leu Val Leu Ala Val Ser Ala Ala Val
1               5                   10                  15

Ala Glu Asn Ala Gly Val Gln Lys Ala Phe Met Asp Ile Glu Ile Asp
            20                  25                  30

Gly Glu Ser Ala Gly Arg Ile Val Leu Glu Leu Arg Gly Asp Val Val
        35                  40                  45

Pro Lys Thr Val Lys Asn Phe Ile Gly Leu Phe Asp Lys Tyr Lys Gly
    50                  55                  60

Ser Thr Phe His Arg Val Ile Ala Asp Phe Met Ile Gln Gly Gly Asp
65                  70                  75                  80

Phe Glu Asn His Asn Gly Thr Gly Gly His Ser Ile Tyr Gly Pro Arg
                85                  90                  95

Phe Glu Asp Glu Asn Phe Thr Leu Lys His Asp Arg Gly Val Ile Ser
            100                 105                 110

Met Ala Asn Ala Gly Pro Asn Thr Asn Gly Ser Gln Phe Phe Ile Thr
        115                 120                 125

Thr Val Lys Thr Glu Trp Leu Asp Gly Arg His Val Val Phe Gly Lys
    130                 135                 140

Ile Thr Asn Asp Ser Trp Pro Thr Val Gln Ala Ile Glu Ala Leu Gly
145                 150                 155                 160

Ser Ser Gly Gly Arg Pro Ser Lys Ile Ala Lys Ile Thr Asp Ile Gly
                165                 170                 175

Leu Leu

<210> SEQ ID NO 3
<211> LENGTH: 28
<212> TYPE: DNA
<213> ORGANISM: Neospora caninum

<400> SEQUENCE: 3
gcatatgaag ctcctgttct tcttcctc                                          28

<210> SEQ ID NO 4
<211> LENGTH: 30
<212> TYPE: DNA
<213> ORGANISM: Neospora caninum

<400> SEQUENCE: 4
agaattctta caacaaacca atgtccgtga                                        30

<210> SEQ ID NO 5
<211> LENGTH: 28
<212> TYPE: DNA
<213> ORGANISM: Neospora caninum

<400> SEQUENCE: 5
ccatatggcg ccgttcaagt cggaaaat                                          28

<210> SEQ ID NO 6
<211> LENGTH: 31
<212> TYPE: DNA
<213> ORGANISM: Neospora caninum -continued

```
<400> SEQUENCE: 6
agaattctca tcctcttaac acgggggaat c                                        31

<210> SEQ ID NO 7
<211> LENGTH: 179
<212> TYPE: PRT
<213> ORGANISM: Neospora caninum

<400> SEQUENCE: 7

Met Lys Leu Val Leu Phe Phe Leu Ala Leu Ala Val Ser Gly Ala Val
1               5                   10                  15

Ala Glu Asn Ala Gly Val Arg Lys Ala Tyr Met Asp Ile Asp Ile Asp
            20                  25                  30

Gly Glu His Ala Gly Arg Ile Ile Leu Glu Leu Arg Glu Asp Ile Ala
        35                  40                  45

Pro Lys Thr Val Lys Asn Phe Ile Gly Leu Phe Asp Lys Tyr Lys Gly
    50                  55                  60

Ser Val Phe His Arg Ile Ile Pro Asp Phe Met Ile Gln Gly Gly Asp
65                  70                  75                  80

Phe Glu Asn His Asn Gly Thr Gly Gly His Ser Ile Tyr Gly Arg Arg
                85                  90                  95

Phe Asp Asp Glu Asn Phe Asp Leu Lys His Glu Arg Gly Val Ile Ser
            100                 105                 110

Met Ala Asn Ala Gly Pro Asn Thr Asn Gly Ser Gln Phe Phe Ile Thr
        115                 120                 125

Thr Val Lys Thr Glu Trp Leu Asp Ala Arg His Val Val Phe Gly Lys
    130                 135                 140

Ile Thr Thr Glu Ser Trp Pro Thr Val Gln Ala Ile Glu Ala Leu Gly
145                 150                 155                 160

Gly Ser Gly Gly Arg Pro Ser Lys Val Ala Lys Ile Thr Asp Ile Gly
                165                 170                 175

Leu Leu Glu
```